(12) United States Patent
Tseng et al.

(10) Patent No.: US 11,262,303 B2
(45) Date of Patent: Mar. 1, 2022

(54) OXYGEN CONTENT SENSOR, OXYGEN CONTENT SENSOR MANUFACTURING METHOD AND USING METHOD

(71) Applicant: National Tsing Hua University, Hsinchu (TW)

(72) Inventors: Fan-Gang Tseng, Hsinchu (TW); Manohar Prasad Koduri, Hsinchu (TW); Yu-Wei Shao, Hsinchu (TW); Venkanagouda S. Goudar, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 38 days.

(21) Appl. No.: 16/441,036

(22) Filed: Jun. 14, 2019

(65) Prior Publication Data

US 2020/0264105 A1    Aug. 20, 2020

(30) Foreign Application Priority Data

Feb. 19, 2019    (TW) .................. 108105481

(51) Int. Cl.
*G01N 21/64* (2006.01)
*G01N 33/52* (2006.01)
*G01N 1/28* (2006.01)
*B82B 3/00* (2006.01)
*B82Y 15/00* (2011.01)
(Continued)

(52) U.S. Cl.
CPC .......... *G01N 21/6428* (2013.01); *B82B 3/00* (2013.01); *G01N 1/28* (2013.01); *G01N 33/52* (2013.01); *B82Y 15/00* (2013.01); *B82Y 40/00* (2013.01); *G01N 31/225* (2013.01); *G01N 2021/0325* (2013.01); *G01N 2021/6439* (2013.01); *G01N 2201/06193* (2013.01)

(58) Field of Classification Search
CPC ...... G01N 21/6428; G01N 33/52; G01N 1/28; G01N 31/225; G01N 2201/06193; G01N 2021/0325; G01N 2021/6439; B82B 3/00; B82Y 40/00; B82Y 15/00
See application file for complete search history.

(56) References Cited

U.S. PATENT DOCUMENTS

2020/0232979 A1* 7/2020 Revzin ............... G01N 21/6428

FOREIGN PATENT DOCUMENTS

| CN | 103575717 | 2/2014 |
|----|-----------|--------|
| CN | 105968372 | 9/2016 |

OTHER PUBLICATIONS

Lin et al. (Jia-Jyun Lin, et al., "Folic acid-Pluronic F127 magnetic nanoparticle clusters for combined targeting, diagnosis, and therapy applications", Oct. 2009, Biomaterials, 30, 28, pp. 5114-5124) (Year: 2009).*

(Continued)

*Primary Examiner* — Samuel P Siefke
*Assistant Examiner* — Henry H Nguyen
(74) *Attorney, Agent, or Firm* — JCIPRNET

(57) ABSTRACT

An oxygen content sensor includes a nanoparticle, a plurality of linkers, and a plurality of fluorescent molecules. The linkers are disposed on the nanoparticle. The fluorescent molecules are arranged on the linkers. The linker has at least a hydrophilic region as well as a hydrophobic region. The linker is linked to the nanoparticle through the hydrophilic region, and the fluorescent molecule is linked to the linker through the hydrophobic region.

6 Claims, 6 Drawing Sheets

(51) Int. Cl.
*B82Y 40/00* (2011.01)
*G01N 31/22* (2006.01)
*G01N 21/03* (2006.01)

(56) References Cited

OTHER PUBLICATIONS

Ruedas-Rama (Maria J. Ruedas-Rama, et al., "Fluorescent nanoparticles for intracellular sensing: A review", Nov. 2012, Analytica Chimica Acts, 751, pp. 1-23) (Year: 2012).*

Grist et al. (Samantha M. Grist, et al, "Optical Oxygen Sensors for Applications in Microfluidic Cell Culture", 2010, Sensors, 10, 9286-9316) (Year: 2010).*

Erik Bland, et al., "Fluorescence ratio imaging for oxygen measurement in a tissue engineered construct," Journal of Histotechnology, vol. 36, Dec. 2013, pp. 1-10.

Yong-Eun Koo Lee, et al., "NIR luminescent oxygen nanosensors with nanoparticle matrix tailored sensitivity," Anal Chem., vol. 82, Oct. 2010, pp. 1-19.

* cited by examiner

OXYGEN CONTENT SENSOR, OXYGEN CONTENT SENSOR MANUFACTURING METHOD AND USING METHOD

CROSS-REFERENCE TO RELATED APPLICATION

This application claims the priority benefit of Taiwan application serial no. 108105481, filed on Feb. 19, 2019. The entirety of the above-mentioned patent application is hereby incorporated by reference herein and made a part of this specification.

BACKGROUND OF THE DISCLOSURE

Field of the Disclosure

The disclosure relates to a sensor, a sensor manufacturing method and using method, and particularly to an oxygen content sensor, an oxygen content sensor manufacturing method and using method.

Description of Related Art

Currently, the image of fluorescent nanoparticles can be successfully formed in cells, and fluorophores can be used to detect the oxygen concentration of the cellular environment. However, few studies have used nanoparticles combined with fluorophores as sensors to monitor and optimize the cellular environment. In addition, studies have shown that by monitoring the specific parameters of the hydrogel environment, the cellular environment information in the hydrogel can be provided immediately, and the cellular environment in the hydrogel can be adjusted to the optimal cellular environment to ensure effective function of cells. In addition, typical commercial sensors may be too large in size, which may affect biocompatibility and cause varying degrees of cytotoxicity.

SUMMARY OF THE DISCLOSURE

The disclosure provides an oxygen content sensor having better cell compatibility, lower cytotoxicity, and lower photo-bleaching effect.

The disclosure provides a manufacturing method for an oxygen content sensor for manufacturing the oxygen content sensor.

The disclosure provides a using method of an oxygen content sensor, which can be applied to a three-dimensional cellular environment, and has the advantage of being easy for calibration.

An oxygen content sensor of the disclosure includes a nanoparticle, a plurality of linkers, and a plurality of fluorescent molecules. The linkers are disposed on the nanoparticle. The fluorescent molecules are arranged on the linkers. The linker has at least a hydrophilic region as well as a hydrophobic region. The linker is linked to the nanoparticle through the hydrophilic region, and the fluorescent molecule is linked to the linker through the hydrophobic region.

In an embodiment of the disclosure, the nanoparticle has a size of 500 nm.

In an embodiment of the disclosure, the linker is a nonionic surfactant.

In an embodiment of the disclosure, the fluorescent molecule is an oxygen sensitive indicator that reacts with oxygen molecules to change the fluorescence intensity.

The manufacturing method of the oxygen content sensor of the disclosure includes the following steps. A nanoparticle is provided. A plurality of linkers are disposed on the nanoparticle. A plurality of fluorescent molecules are disposed on the linker. Specifically, the linker has at least a hydrophilic region and a hydrophobic region. The linker is linked to the nanoparticle through the hydrophilic region, and the fluorescent molecule is linked to the linker through the hydrophobic region.

In an embodiment of the disclosure, the manufacturing method of the oxygen content sensor further includes the following steps. The nanoparticle is surface-modified before the linker is disposed on the nanoparticle so that the surface of the nanoparticle has a carboxylic functional group.

In an embodiment of the disclosure, the step of linking the hydrophilic region the linker to the nanoparticle includes an esterification reaction.

In an embodiment of the disclosure, the fluorescent molecule is linked to the hydrophobic region of the linker in a hydrophobic interaction.

The using method of the oxygen content sensor of the disclosure includes the following steps. First, a first hydrogel is formed, and the first hydrogel is coated with the cells and the oxygen content sensor. Next, the cells in the first hydrogel are cultured. Then, the first fluorescence intensity of the oxygen content sensor in the first hydrogel is detected. Then, the oxygen content in the first hydrogel is calculated based on the first fluorescence intensity and the oxygen content-fluorescence intensity relationship curve diagram.

In an embodiment of the disclosure, the manufacturing step of the oxygen content-fluorescence intensity relationship curve diagram includes the following steps. First, a second hydrogel is formed and the second hydrogel is coated with the oxygen content sensor. Next, various environments with different oxygen concentrations are provided. Then, the second fluorescence intensity of the oxygen content sensor in the second hydrogel is detected respectively under the environments with these oxygen concentrations. Then, an oxygen content-fluorescence intensity relationship curve diagram is established based on the oxygen concentration and the corresponding second fluorescence intensity.

Based on the above, in the oxygen content sensor, the manufacturing method and using method of the oxygen content sensor of the disclosure, the oxygen content sensor includes a nanoparticle, a plurality of linkers, and a plurality of fluorescent molecules. Specifically, the linker is disposed on the nanoparticle, and the fluorescent molecule is disposed on the linker. The linker is linked to the nanoparticle through its hydrophilic region, and the fluorescent molecule is linked to the linker through the hydrophobic region of the linker. In this manner, the oxygen content sensor of the disclosure has better cell compatibility, lower cytotoxicity, and lower photo-bleaching effect, such that the using method of the oxygen content sensor of the disclosure can apply the oxygen content sensor to a three-dimensional environment for culturing cells and has the advantage of being easy for calibration.

In order to make the aforementioned features and advantages of the disclosure more comprehensible, embodiments accompanying figures are described in detail below.

DESCRIPTION OF EMBODIMENTS

Figure 1A:
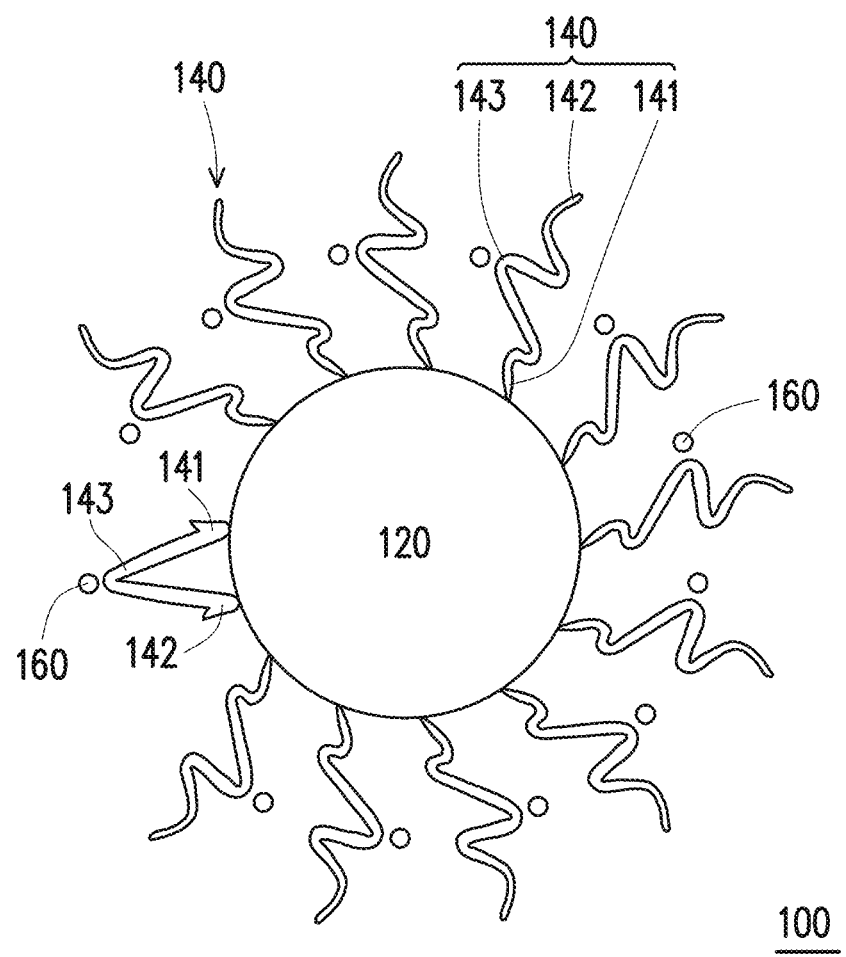
FIG. 1A is a schematic view of an oxygen content sensor according to an embodiment of the disclosure.
Figure 1B:
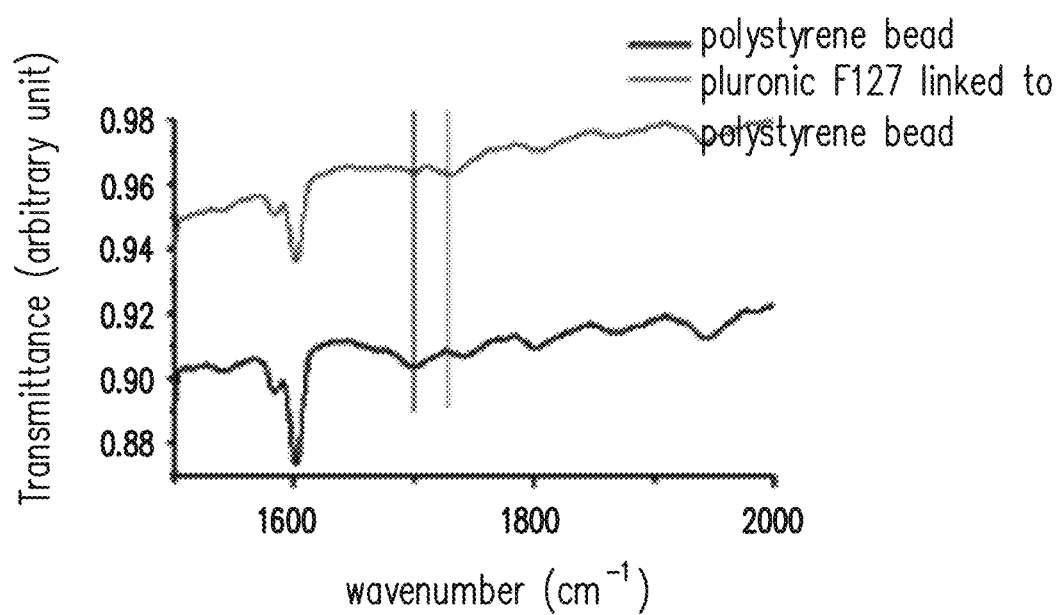
FIG. 1B is an analysis diagram of Fourier transform infrared spectrometry according to an embodiment of the disclosure.
Figure 1C:
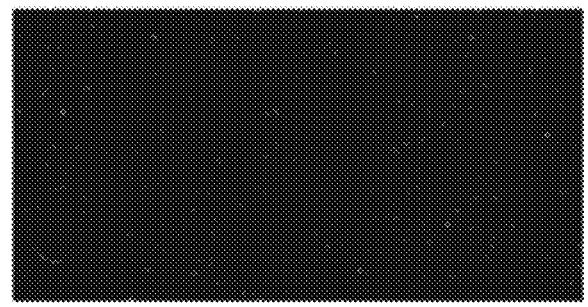
FIG. 1C is a fluorescent image diagram of an embodiment of the disclosure.

FIG. 1A is a schematic view of an oxygen content sensor according to an embodiment of the disclosure. FIG. 1B is an analysis diagram of Fourier transform infrared spectrum according to an embodiment of the disclosure. FIG. 1C is a fluorescent image diagram of an embodiment of the disclosure.

Referring to FIG. 1A, an oxygen content sensor 100 of the present embodiment includes a nanoparticle 120, a plurality of linkers 140, and a plurality of fluorescent molecules 160. The linker 140 is disposed on the nanoparticle 120. The fluorescent molecule 160 is disposed on the linker 140. The linker 140 has at least hydrophilic regions 141, 142 and a hydrophobic region 143. The hydrophilic region 141 and the hydrophilic region 142 are respectively located at both ends of the linker 140, and the hydrophobic region 143 is located in the middle of the linker 140. The linker 140 can be linked to the nanoparticle 120 through the hydrophilic region 141 (and/or the hydrophilic region 142), and the fluorescent molecule 160 can be linked to the linker 140 through the hydrophobic region 143.

In the present embodiment, the nanoparticle 120 is, for example, a polystyrene bead (PSB), but is not limited thereto. The size of the nanoparticle 120 is, for example, 500 nm, but is not limited thereto. It should be noted that, in the embodiment, when the size of the nanoparticle 120 in the oxygen content sensor 100 is 500 nm, the oxygen content sensor 100 has less cytotoxicity and better biocompatibility to cells.

In this embodiment, the linker 140 is a nonionic surfactant. In some embodiments, the linker 140 is, for example, a pluronic F127, but is not limited thereto. The pluronic F127 is a triblock copolymer of poly(ethylene oxide)-poly (propylene oxide-poly(ethylene oxide) (PEO-PPO-PEO). Specifically, the poly(ethylene oxide) is located at both ends of the pluronic F127 and is hydrophilic, and the poly (propylene oxide) is located in the middle of the pluronic F127 and is hydrophobic. That is to say, the pluronic F127 is an amphiphilic block copolymer with both hydrophilicity and hydrophobicity.

In this embodiment, the fluorescent molecule 160 is an oxygen sensitive indicator that reacts with oxygen molecules to change its fluorescence intensity. In some embodiments, the fluorescent molecule 160 is, for example, $Ru(dpp)_3Cl_2$ ($C_{72}H_{48}Cl_2N_6Ru$), but is not limited thereto. The excitation light of $Ru(dpp)_3Cl_2$ has a wavelength of 470-490 nm, and the wavelength of the emitted light is 613 nm (red fluorescence).

In this embodiment, the manufacturing method of the oxygen content sensor 100 may include the following steps. First, a nanoparticle 120 is provided. Next, the nanoparticle 120 is surface-modified such that the surface of the nanoparticle has a carboxylic functional group. Then, a plurality of linkers 140 are disposed on the nanoparticle 120, and a plurality of fluorescent molecules 160 are disposed on the linker 140. Specifically, since the linker 120 has at least the hydrophilic regions 141, 142 and the hydrophobic region 143, the linker 120 can be linked to the nanoparticle 120 through its hydrophilic region 141 (and/or the hydrophilic region 142), and the fluorescent molecule 160 can be linked to the linker 140 through the hydrophobic region 143.

Specifically, in the present embodiment, 0.5 ml of polystyrene bead solution (100 mg/ml) was first centrifuged at 8000 rpm for 10 minutes to retrieve polystyrene beads from a sodium azide solution. Next, in order to obtain a relatively pure polystyrene bead, a purification step was repeated twice. The purification step was performed as follows: deionized water is mixed with the polystyrene bead and centrifuged at 8000 rpm for 10 minutes to remove the supernatant liquid. After the purification step was performed twice, the deionized water was added to make a polystyrene bead solution in an amount of 1 ml. Then, the pluronic F127 (0.1 g/1 ml of polystyrene bead solution) was added and reacted at room temperature for 2 hours to allow the pluronic F127 to be linked to the surface of the polystyrene bead. Specifically, since the poly(ethylene oxide) (hydrophilic region) in the pluronic F127 can be esterified with the carboxylic functional group on the surface of the polystyrene bead, a bond can be formed to link the pluronic F127 to the polystyrene bead. On this occasion, 1 ml of a solution (abbrev. PSB-F127) of the pluronic F127 linked to the polystyrene bead was obtained. Therefore, please refer to the analysis diagram of Fourier transform infrared spectrometry (FTIR) in FIG. 1B, which shows the infrared transmittance of the polystyrene bead solution and PSB-F127 at different wavenumbers. Based on the result shown in FIG. 1B, it can be obtained that when the wavenumber is about 1700 $cm^{-1}$, as compared to the polystyrene bead solution, the spectrum chart of PSB-F127 has an additional peak, which indicates that the pluronic F127 has indeed been successfully linked to polystyrene bead.

Next, 1 mg of $Ru(dpp)_3Cl_2$ was dissolved in 200 μl of 99.5% pure ethanol, and an ethanol solution containing $Ru(dpp)_3Cl_2$ was added to the 1 ml of PSB-F127 previously prepared. Ultrasonic treatment was carried out for at least 30 minutes so that $Ru(dpp)_3Cl_2$ can be linked to poly(propylene oxide) (hydrophobic region) in the pluronic F127 through hydrophobic interaction, thereby forming the functional oxygen content sensor 100. Referring to FIG. 1C, when the functional oxygen content sensor 100 receives the excitation light having a wavelength of 470 nm, red fluorescence having a wavelength greater than 610 nm can be observed, indicating that $Ru(dpp)_3Cl_2$ has indeed been successfully linked to the PSB-F127.

Then, the functional oxygen content sensor 100 was washed with sterile deionized water and centrifuged at 8000 rpm for 10 minutes to remove the supernatant liquid. Finally, 1 ml of sterile deionized water was added to the washed oxygen content sensor 100 and stored in a dark and dry place at room temperature. So far, the oxygen content sensor 100 of the present embodiment has been completed.

The using method of the oxygen content sensor of the present embodiment will be described below. For example, in the present embodiment, the oxygen content sensor 100 can be coated in the hydrogel, and then the change of oxygen content in the hydrogel can be calculated through the change of fluorescence intensity of the oxygen content sensor 100.

Figure 2A:
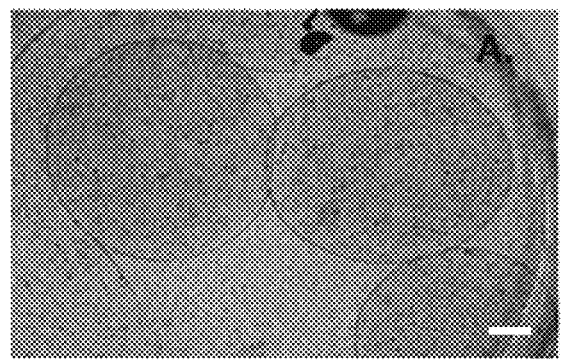
FIG. 2A shows a second hydrogel in a bright field according to an embodiment of the disclosure.
Figure 2B:
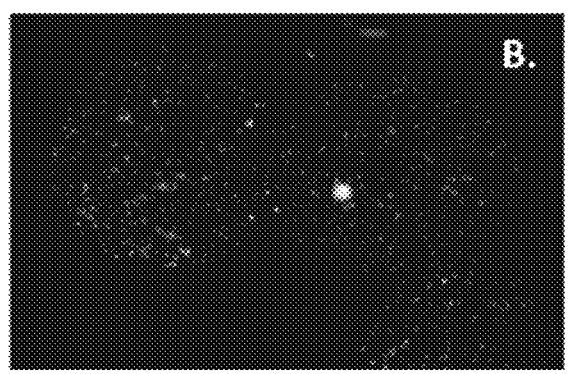
FIG. 2B is a fluorescent image of a second hydrogel according to an embodiment of the disclosure.
Figure 2C:
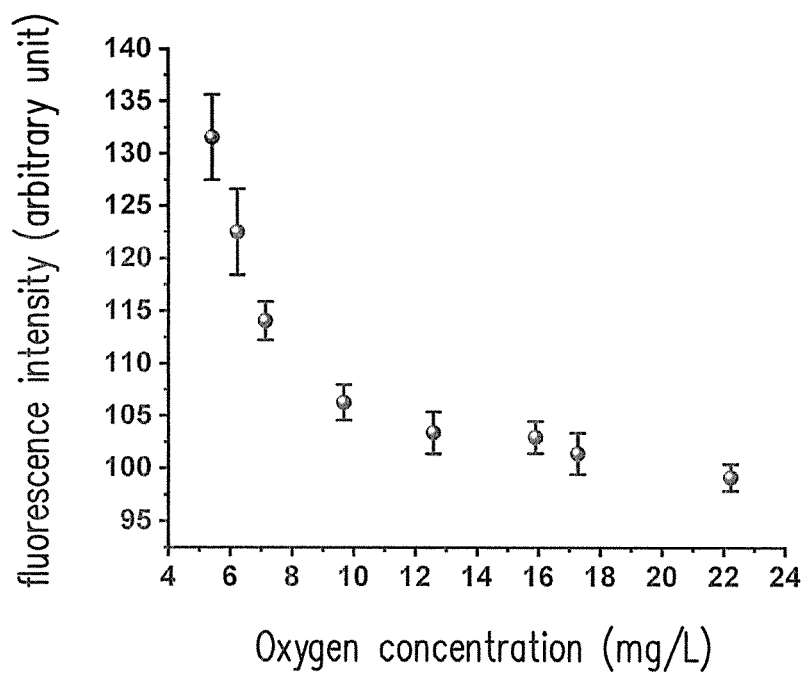
FIG. 2C is a curve diagram showing an oxygen content-fluorescence intensity relationship according to an embodiment of the disclosure.
Figure 2D:
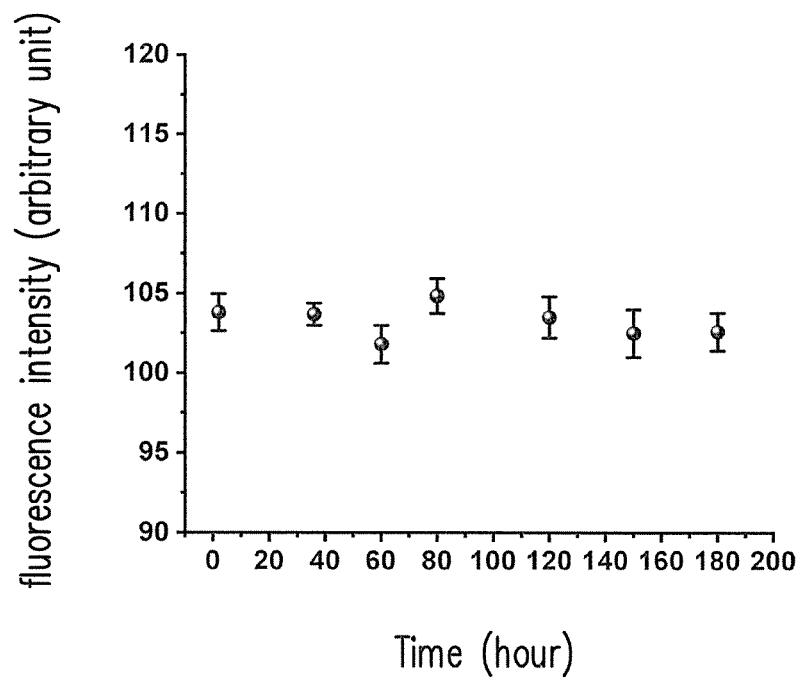
FIG. 2D is a relationship diagram between the fluorescence intensity and the elapsed time in an environment of the same oxygen concentration according to an embodiment of the disclosure.

FIG. 2A shows a second hydrogel in a bright field according to an embodiment of the disclosure. FIG. 2B is a fluorescent image of a second hydrogel according to an embodiment of the disclosure. FIG. 2C is a curve diagram showing an oxygen content-fluorescence intensity relationship according to an embodiment of the disclosure. FIG. 2D is a relationship diagram between the fluorescence intensity and the elapsed time in an environment of the same oxygen concentration according to an embodiment of the disclosure.

Please refer to FIG. 2C first. In this embodiment, the oxygen content-fluorescence intensity relationship curve diagram in FIG. 2C should be prepared first so that it is possible to calculate the oxygen content corresponding to any fluorescence intensity by using the oxygen content-fluorescence intensity relationship curve diagram. Specifically, in the present embodiment, the oxygen content-fluorescence intensity relationship curve diagram can be made through the following steps. First, the oxygen content sensor 100 is mixed with alginate, and an alginate-filled hydrogel is formed by electrospraying. For example, 20 µl of oxygen content sensor 100 can be mixed with 10 ml of 3% alginate. Next, calcium chloride or strontium chloride as a crosslinking agent is added for curing to obtain a second hydrogel. Specifically, the second hydrogel is coated with the oxygen content sensor 100 but is not coated with cells as shown in FIG. 2A and FIG. 2B. FIG. 2A shows observation of a second hydrogel in which the oxygen content sensor 100 is coated under a bright field. FIG. 2B shows observation of a fluorescent image of the second hydrogel in which the oxygen content sensor 100 is coated when the excitation light having a wavelength of 470 nm is applied. The scale bar in FIG. 2A is 200 nm.

Next, various environments with different oxygen concentrations (mg/L) were provided, and the second fluorescence intensity of the oxygen content sensor 100 in the second hydrogel was detected under the environments with these oxygen concentrations, respectively. Then, based on the oxygen concentration and the corresponding second fluorescence intensity, an oxygen content-fluorescence intensity relationship curve diagram was established as shown in FIG. 2C. As can be seen from FIG. 2C, as the oxygen concentration in the environment increased, the second fluorescent intensity of the oxygen content sensor 100 in the second hydrogel decreased. That is, the oxygen content sensor 100 in the second hydrogel can exhibit a good wide dynamic range (about 2.73-22.23 mg/L) and a resolution of −0.01 mg/L with respect to different oxygen concentrations. Therefore, the accuracy of the oxygen content sensor 100 of the present embodiment may be about ±4%.

Furthermore, in order to exclude photo-bleaching effect from the main cause of the decrease in the second fluorescence intensity of the oxygen content sensor 100 in the second hydrogel, the second hydrogel was placed in an environment of the same oxygen concentration for a long time, and the corresponding second fluorescence intensity was measured regularly, thereby illustrating a relationship diagram between the fluorescence intensity and the elapsed time as shown in FIG. 2D. The result of FIG. 2D shows that there was no significant difference in the second fluorescence intensity of the oxygen content sensor 100 in the second hydrogel after about 180 hours, which indicates that the oxygen content sensor 100 in the present embodiment has good structural stability and has a low photo-bleaching effect.

Figure 3A:
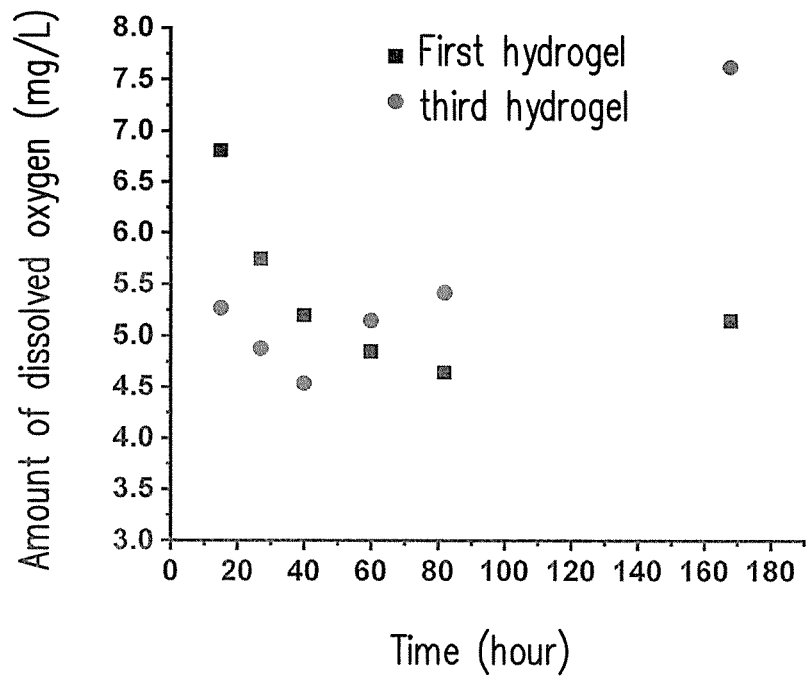
FIG. 3A is a relationship diagram between the amount of dissolved oxygen and the elapsed time in a hydrogel containing cells according to an embodiment of the disclosure.
Figure 3B:
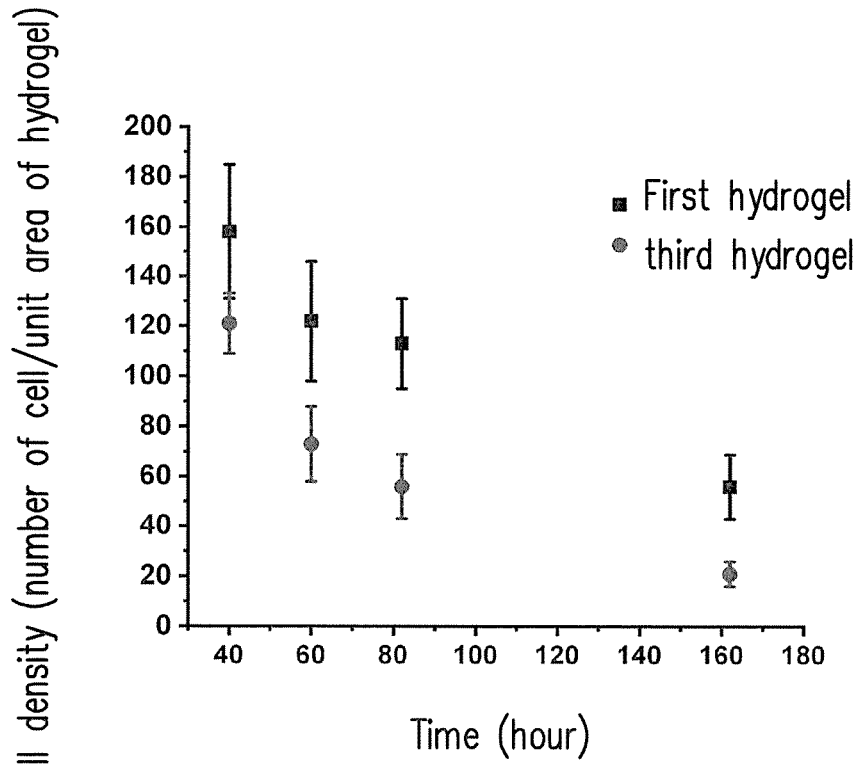
FIG. 3B is a relationship diagram between the cell density and the elapsed time in a hydrogel containing cells according to an embodiment of the disclosure.

FIG. 3A is a relationship diagram between the amount of dissolved oxygen and the elapsed time in a hydrogel containing cells according to an embodiment of the disclosure. FIG. 3B is a relationship diagram between the cell density and the elapsed time in a hydrogel containing cells according to an embodiment of the disclosure.

Referring to FIG. 3A, in the present embodiment, the oxygen content in the hydrogel in which the oxygen content sensor 100 and the cells were coated simultaneously is detected at different culture times. Specifically, the oxygen content sensor 100, RIN-m5F cells ($2.00 \times 10^6$ cells/ml), and alginate were mixed, and an alginate-filled hydrogel was formed by electrospraying. Next, calcium chloride or strontium chloride as a crosslinking agent may be separately added for curing. Thus, the first hydrogel can be obtained by curing with calcium chloride, and the third hydrogel can be obtained by curing with strontium chloride. Specifically, the oxygen content sensor 100 and about 700 to 800 RIN-m5F cells were coated in the first hydrogel cured through calcium chloride, and the oxygen content sensor 100 and about 700 to 800 RIN-m5F cells were coated in the third hydrogel cured through strontium chloride.

Then, the generated first hydrogel or third hydrogel was collected by using a pipette tip, respectively, and the first hydrogel or the third hydrogel is uniformly distributed in a 96-well plate, respectively. Next, cell culture was carried out in an environment of 37° C. with 5% carbon dioxide, and the fluorescence intensity was measured at a specific time point. Specifically, the first fluorescent intensity can be measured at a specific time point in the first hydrogel, and the third fluorescent intensity can be measured at a specific time point in the third hydrogel. Then, as shown in FIG. 3A, the oxygen content (amount of dissolved oxygen) in the first hydrogel at a specific time point can be calculated based on the first fluorescence intensity and the established oxygen content-fluorescence intensity relationship curve diagram. Likewise, the oxygen content (amount of dissolved oxygen) in the third hydrogel at a specific time point can be calculated based on the third fluorescence intensity and the established oxygen content-fluorescence intensity relationship curve diagram. Thus, as can be seen from the result of FIG. 3A, the oxygen content in the first hydrogel decreased with time within 80 hours; and there was a gradual increase in the oxygen content in the first hydrogel between 80 and 170 hours. In addition, similar to the case of the first hydrogel, the oxygen content in the third hydrogel decreased with time within 40 hours; and there was a gradual increase in the oxygen content in the third hydrogel between 40 and 170 hours.

It should be noted that, in the FIG. 3A, presumably the condition where the oxygen content in the first hydrogel or the third hydrogel is first decreased and then increased is probably related to the cell intensity (shown in FIG. 3B) in the first hydrogel or the third hydrogel. That is, when the cell density in the first hydrogel is high, the oxygen consumption of the cells is greater than the amount of oxygen diffused into the first hydrogel from outside of the first hydrogel, and thus the oxygen content in the first hydrogel is decreased with time. On the contrary, when the cell density in the first hydrogel is decreased gradually, the oxygen consumption of the cells is gradually lower than the amount of oxygen diffused into the first hydrogel from outside of the first hydrogel, and thus the oxygen content in the first hydrogel is increased with time. Likewise, when the cell intensity in the third hydrogel is high, the oxygen consumption of the cells is greater than the amount of oxygen diffused into the third hydrogel from outside of the third hydrogel, and thus the oxygen content in the third hydrogel is decreased with time. On the contrary, when the cell density in the third hydrogel is decreased gradually, the oxygen consumption of the cells is gradually lower than the amount of oxygen diffused into the third hydrogel from outside of the third hydrogel, and thus the oxygen content in the third hydrogel is increased with time.

Referring to FIG. 3B, living cells were dyed with calcein-AM fluorescent dye to calculate the cell density (cell number/unit area of hydrogel) of living cells. As can be seen from the result of FIG. 3B, the cell density in the first hydrogel (or the third hydrogel) presents exponential decay with time.

Figure 4A:
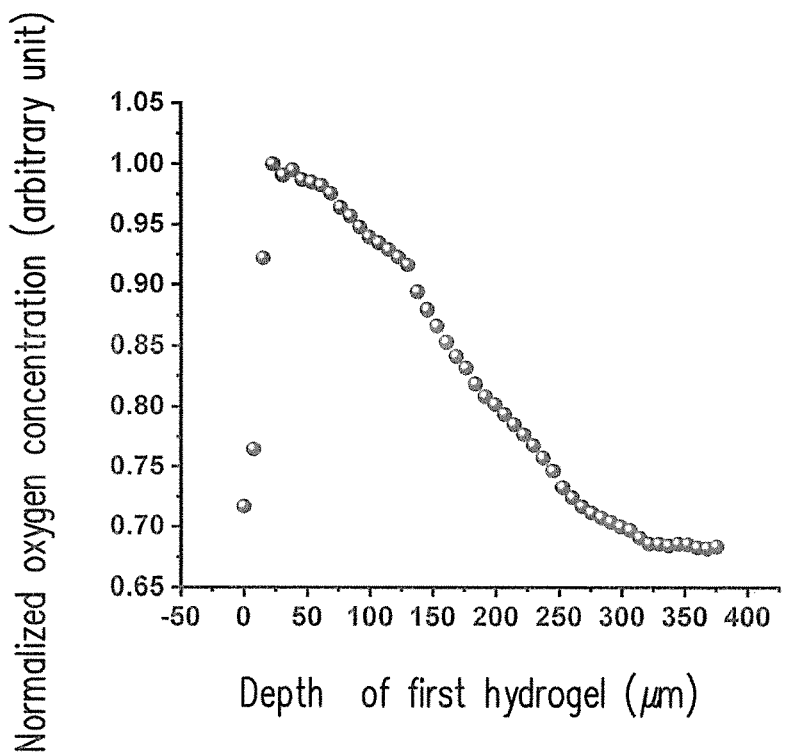
FIG. 4A-FIG. 4B are relationship diagrams between the normalized oxygen concentration and depth of a hydrogel in a hydrogel containing cells according to an embodiment of the disclosure.
Figure 4B:
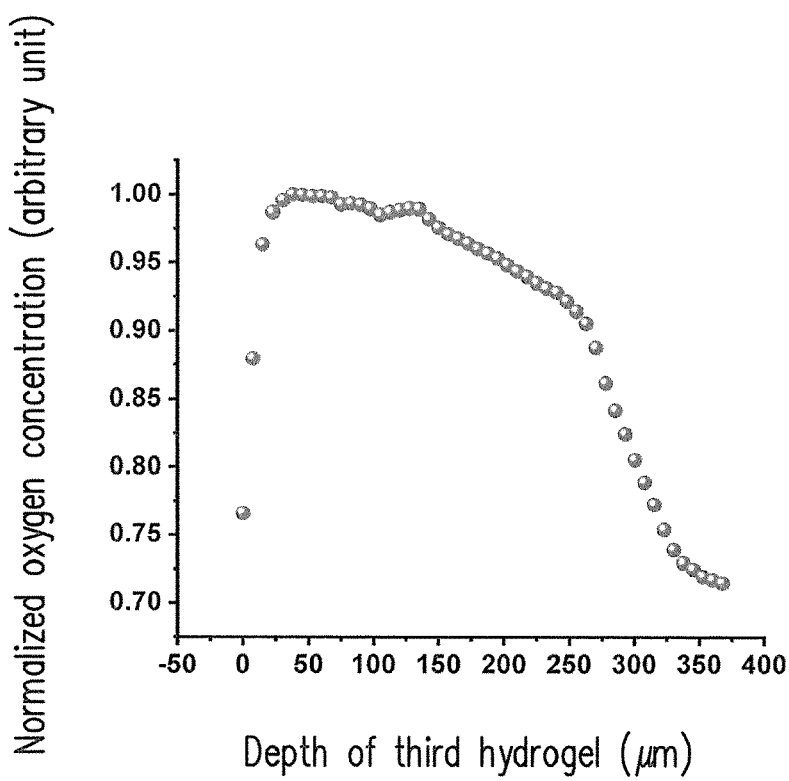

FIG. 4A-FIG. 4B are relationship diagrams between the normalized oxygen concentration and depth of a hydrogel in a hydrogel containing cells according to an embodiment of the disclosure.

Referring to FIG. 4A and FIG. 4B, after three days (about 84 hours) of cell culture, the fluorescence intensity corresponding to the different depths inside the first hydrogel or the third hydrogel was detected by using a confocal microscope. Next, the corresponding fluorescence intensity is converted into oxygen content, the highest oxygen content value is normalized to 1, and the other oxygen content values are normalized with respect to the highest oxygen content value. As can be seen from the result of FIG. 4A, the normalized oxygen concentration presents a gradient change from the exterior (about 0 micrometer in depth) of the first hydrogel to the center (about 350 micrometers in depth) of the interior. The result of FIG. 4B shows that the normalized oxygen concentration presents a gradient change from the exterior (about 0 micrometer in depth) of the third hydrogel to the center (about 350 micrometers in depth) of the interior.

It should be noted that although the oxygen content sensor 100 of the present embodiment is used to detect changes in oxygen content in the hydrogel, which should not be restricted as a limitation to the disclosure. That is, in other embodiments, the oxygen content sensor can also be used in other environments to detect changes in oxygen content in other environments.

In summary, in the oxygen content sensor, the manufacturing method and using method of the oxygen content sensor of the disclosure, the oxygen content sensor includes a nanoparticle, a plurality of linkers, and a plurality of fluorescent molecules. Specifically, the linker is disposed on the nanoparticle, and the fluorescent molecule is disposed on the linker. The linker is linked to the nanoparticle through its hydrophilic region, and the fluorescent molecule is linked to the linker through the hydrophobic region of the linker. In this manner, the oxygen content sensor of the disclosure has better cell compatibility, lower cytotoxicity, and lower photo-bleaching effect, such that the using method of the oxygen content sensor of the disclosure can apply the oxygen content sensor to a three-dimensional environment for culturing cells and has the advantage of being easy for calibration.

Although the disclosure has been disclosed by the above embodiments, the embodiments are not intended to limit the disclosure. It will be apparent to those skilled in the art that various modifications and variations can be made to the structure of the disclosure without departing from the scope or spirit of the disclosure. Therefore, the protecting range of the disclosure falls in the appended claims.

What is claimed is:

1. An oxygen content sensor, comprising:
   a nanoparticle, wherein the nanoparticle is a polystyrene bead, and the nanoparticle has a size of 500 nm;
   a plurality of linkers disposed on the nanoparticle; and
   a plurality of fluorescent molecules, disposed on the plurality of linkers, wherein each of the plurality of linkers has a first hydrophilic region, a second hydrophilic region and a hydrophobic region, the plurality of linkers are linked to the nanoparticle through the first hydrophilic region, the plurality of fluorescent molecules are linked to the plurality of linkers through the hydrophobic region, and the second hydrophilic region is linked to the nanoparticle or dangling,
   wherein the plurality of fluorescent molecules are oxygen sensitive indicators capable of reacting with oxygen molecules to change a fluorescence intensity.

2. The oxygen content sensor according to claim 1, wherein the plurality of linkers are nonionic surfactants.

3. A manufacturing method of an oxygen content sensor, comprising:
   providing a nanoparticle, wherein the nanoparticle is a polystyrene bead, and the nanoparticle has a size of 500 nm;
   disposing a plurality of linkers on the nanoparticle; and
   disposing a plurality of fluorescent molecules on the plurality of linkers, wherein each of the plurality of linkers has a first hydrophilic region, a second hydrophilic region and a hydrophobic region, the plurality of linkers are linked to the nanoparticle through the first hydrophilic region, the plurality of fluorescent molecules are linked to the plurality of linkers through the hydrophobic region, and the second hydrophilic region is linked to the nanoparticle or dangling.

4. The manufacturing method of the oxygen content sensor according to claim 3, further comprising:
   surface-modifying the nanoparticle before disposing the plurality of linkers on the nanoparticle such that a surface of the nanoparticle has a carboxylic functional group.

5. The manufacturing method of the oxygen content sensor according to claim 3, wherein the step of linking the first hydrophilic region of the plurality of linkers to the nanoparticle comprises an esterification reaction.

6. The manufacturing method of the oxygen content sensor according to claim 3, wherein the plurality of fluorescent molecules are linked to the hydrophobic region of the plurality of linkers through a hydrophobic interaction.

* * * * *